United States Patent [19]

Öhlin

[11] Patent Number: 5,731,211
[45] Date of Patent: Mar. 24, 1998

[54] METHOD AND APPARATUS FOR ANALYSING A LIQUID SAMPLE

[75] Inventor: Erik Öhlin, Stocksund, Sweden

[73] Assignee: Swelab Instrument AB, Stockholm, Sweden

[21] Appl. No.: 666,494

[22] PCT Filed: Jan. 10, 1995

[86] PCT No.: PCT/SE95/00012

§ 371 Date: Jul. 10, 1996

§ 102(e) Date: Jul. 10, 1996

[87] PCT Pub. No.: WO95/18962

PCT Pub. Date: Jul. 13, 1995

[30] Foreign Application Priority Data

Jan. 10, 1994 [SE] Sweden .................. 9400032

[51] Int. Cl.$^6$ ...................................... G01N 1/38
[52] U.S. Cl. .............. 436/179; 436/52; 436/174; 436/180; 422/68.1; 422/81
[58] Field of Search ............. 436/43, 49, 174, 436/179, 180; 422/63, 67, 68.1, 81, 100; 73/864.21, 864.22, 864.23, 864.24, 864.81

[56] References Cited

U.S. PATENT DOCUMENTS

| 3,419,358 | 12/1968 | Smythe et al. ............. 436/179 |
| 3,912,393 | 10/1975 | Hossom et al. ............. 356/36 |
| 4,512,953 | 4/1985 | Marsoner et al. ............. 422/67 |
| 4,522,493 | 6/1985 | Tamagawa et al. ............. 356/36 |
| 4,640,821 | 2/1987 | Mody et al. ............. 422/81 |
| 4,837,161 | 6/1989 | Stevens et al. ............. 436/52 |
| 4,997,627 | 3/1991 | Bergkuist et al. ............. 422/81 |
| 5,192,509 | 3/1993 | Surjaatmadja et al. ............. 422/75 |
| 5,221,521 | 6/1993 | Hashizume et al. ............. 422/100 |
| 5,480,614 | 1/1996 | Kamahori ............. 422/70 |

FOREIGN PATENT DOCUMENTS

| 0 081 919 | 6/1983 | European Pat. Off. . |
| 0 089 937 | 9/1983 | European Pat. Off. . |
| 33 35 641 | 5/1984 | Germany . |

Primary Examiner—Long V. Le
Attorney, Agent, or Firm—Hill, Steadman & Simpson

[57] ABSTRACT

In a method and apparatus for analyzing a liquid sample, particularly a sample of blood, in different concentrations, a portion of a sample contained in a sample receptacle (P) and diluted to a predetermined concentration is again diluted to a predetermined lower concentration when it is transferred to a receiving vessel (20) in which the sample is analyzed in respect of one or more sample parameters. The transfer is effected by a pipette (17) which in a first position (B) thereof is brought together with the sample receptacle (P) for aspiration of said sample portion and which is then shifted to a second position (A) for dispensing the portion and liquid diluent to the receiving vessel (20). The sample receptacle is then brought together with a device (33, 25) for adding a predetermined quantity of liquid to the remainder of the sample in the sample receptacle (P) and for subsequent transfer of the sample from the sample receptacle to the receiving vessel (20) in which the sample is analyzed in respect of one or more additional parameters.

21 Claims, 1 Drawing Sheet

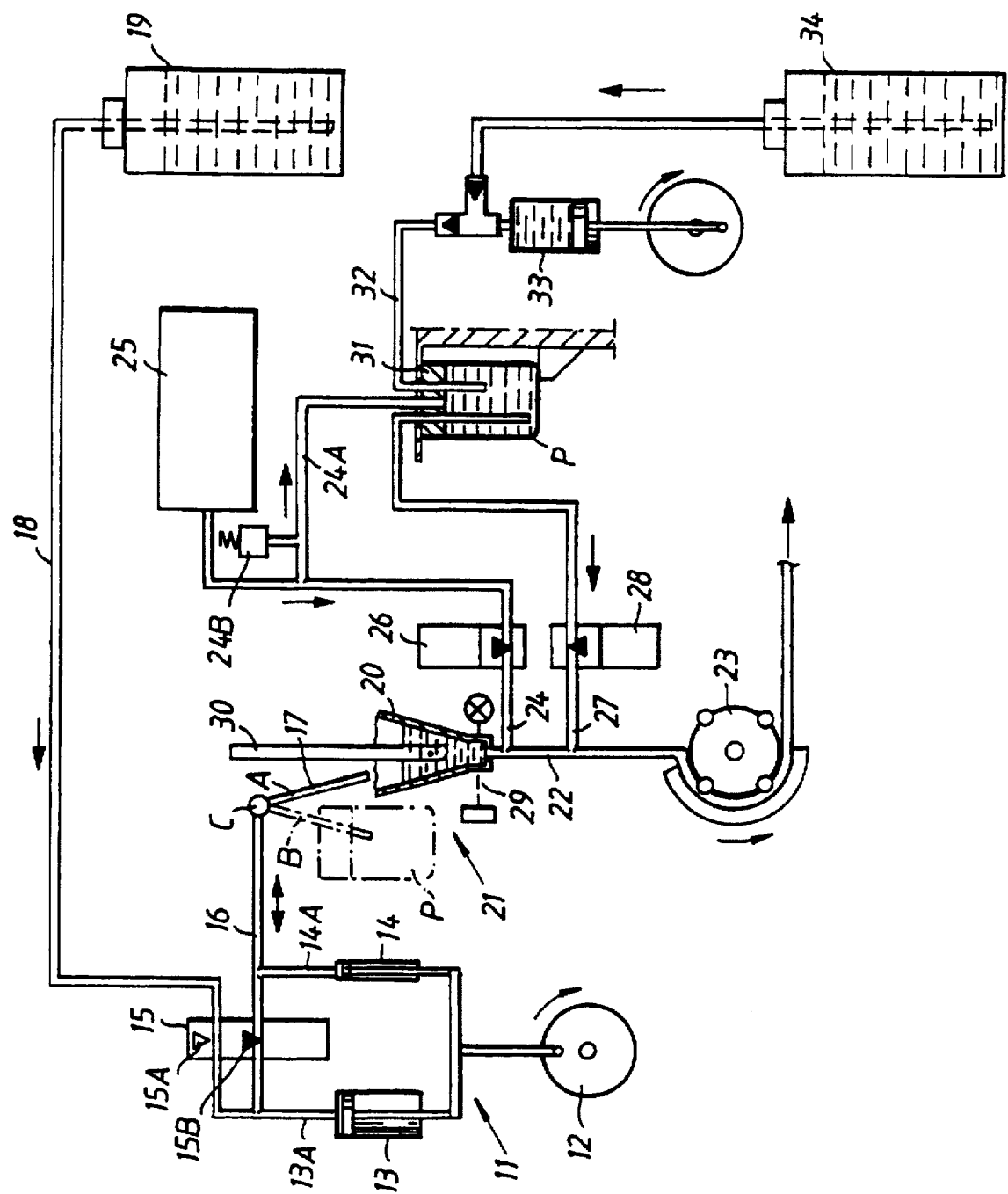

METHOD AND APPARATUS FOR ANALYSING A LIQUID SAMPLE

This invention relates to a method for analysing a liquid sample, preferably in different dilutions, in which a sample contained in a sample receptacle is diluted to a predetermined concentration.

When testing blood in respect of different characteristic parameters or properties it is common practice to prepare from a sample of whole blood two or more subsamples which are diluted to different predetermined dilutions or concentrations. A test which requires dilution to at least two widely differing concentrations may be directed, for example, to determinations of parameters of red blood cells and blood platelets carried out on a subsample diluted to a first, low dilution (high concentration) and to determinations of parameters of white blood cells and haemoglobin carried out on a subsample diluted to a second, substantially higher dilution (lower concentration).

Generally, the subsamples are prepared by first diluting the sample of whole blood, or a portion thereof, to the low dilution in a first vessel for forming a first subsample. A portion of the first subsample is transferred to a second vessel together with a predetermined volume, e.g. 200 times the volume of the transferred subsample portion, of a diluent for forming a second subsample. An example of such serial dilution and apparatus for performing it is disclosed in U.S. Pat. No. 4,746,491.

An object of the invention is to provide a method of the nature indicated above which can be performed rapidly and by simple apparatus in an automated analyser.

To this end, there is provided according to the invention a method and apparatus having the characterising features set forth in the independent claims. The dependent claims define preferred embodiments of the method and apparatus.

BRIEF DESCRIPTION OF THE DRAWING

The invention will be described in greater detail below with reference to the accompanying diagrammatic drawing which illustrates an example of an apparatus for carrying out an embodiment of the method according to the invention.

The analyser illustrated diagrammatically in the drawing is adapted for serial examination of blood samples, namely for analysing each blood sample in respect of the number of red blood cells, the number of white blood cells and the number of platelets per unit volume to the sample and also the haemoglobin content and additional characteristic parameters or properties.

The analyser comprises a dual piston pump, generally designated by 11, which comprises a drive mechanism 12 driving a pair of piston pumps 13 and 14 serving as volume metering devices, and a valve mechanism 15. Piston pump 13 comprises a common inlet and outlet passage 13A and has a stroke volume which is substantially greater, 200 times greater, than the stroke volume of piston pump 14, which likewise comprises a common inlet and outlet passage 14A.

By way of a common conduit 16 the inlet-outlet passages 13A and 14A of both pumps 13, 14 are connected with one end of a pipette tube 17. A supply conduit 18, which can be blocked by means of a valve 15A of valve device 15, extends from a supply container 19 for isotonic diluent to the inlet-outlet passage 13A of pump 13. A section of the common conduit 16 extends between inlet-outlet passage 13A and inlet-outlet passage 14A and can be blocked by means of a valve 15B of valve device 15.

Pipette tube 17 is mounted on the body or housing (not shown) of the analyser such that it can take either of two predetermined positions, namely a position for aspirating a sample from a sample receptacle and a position for dispensing the aspirated sample to a receiving vessel together with a liquid diluent as will be described below. In the drawing, the pipette tube 17 is shown in full lines in the dispensing position at A, while it is shown in phantom lines in the aspirating position at B. A beaker-type sample receptacle P, into which the free end of the pipette tube 17 extends, is also indicated in phantom lines at the aspirating position. Shifting of the pipette tube 17 between positions A and B takes place by pivotal movement about a horizontal axis C and can be effected manually or automatically.

The receiving vessel, which is designated by 20, is open at the top and positioned in relation to the pipette tube 17 such that in the dispensing position A the free end of the pipette tube is above or in the receiving vessel. Receiving vessel 20 forms part of an instrument, generally designated by 21, which operates in well-known manner to analyse blood in respect of the number of red and white blood cells and platelets per unit volume of blood, the size distribution of the blood cells, the haematocrit and the haemoglobin content of the blood and other characteristic parameters or properties. This instrument may be, for example, the instrument which is produced and marketed under the designation SWELAB AutoCounter AC900 series by the assignee of the present invention.

At the bottom thereof, receiving vessel 20 is connected to a waste conduit 22 extending to a drain pump 23, to an air conduit 24, which extends to a pulsating air pump 25 and can be blocked by means of a valve 26, and to a liquid supply conduit 27, which can be blocked by means of a valve 28.

The lower portion of receiving vessel 20 forms a cuvette of a photometric haemoglobinometer which is diagrammatically indicated at 29 and is incorporated in instrument 21.

A measuring tube 30 of well-known type, which also forms part of instrument 21 and is used for counting and other examination of blood cells in accordance with conventional techniques, extends into the receiving vessel 20. In the wall thereof, measuring tube 30 has a microscopic measuring aperture through which a heavily diluted suspension of blood cells is passed during the examination. The impedance changes occurring across the measuring aperture when blood cells pass through it are detected and result in electric impulses the number and amplitudes of which are representative of the number and volume of the blood cells.

A beaker mount 31, suitably provided externally on the analyser body or housing (not shown) is adapted to hold and seal the beaker-like sample receptacle P. Through the portion of the beaker mount 31 which serves to seal the sample receptacle P extend the above-mentioned liquid supply conduit 27, the inlet end of which is positioned near the bottom of the sample receptacle when the latter is held by the beaker mount, a branch 24A of the air conduit 24, and a further conduit 32 leading from a dispensing device 33 for a liquid reagent that haemolyses red blood cells. Dispensing device 33 is a piston pump device of known construction, the inlet conduit of which is connected to a reagent supply container 34.

The analysis of a blood sample in accordance with the method of the invention and using the above-described apparatus will now be described in greater detail. Starting point for the description is the situation in which the analysis of a preceding sample is completed and the sample has been removed from receiving vessel 20 which, however, still contains rinsing liquid.

From the sample of blood to be analysed there is initially prepared a diluted sample (dilution 1:200, for example) in a sample receptacle P. This preparation may be carried out in different ways, e.g. when drawing the sample by introducing a predetermined, precisely measured quantity of the blood in a sample receptacle which has been factory-filled with a predetermined quantity (4 ml. for example) of isotonic solution under sterile conditions and sealed such that the sterility is preserved during storage.

Pipette tube 17, which is initially in the dispensing position A, i.e. the position shown in full lines in the drawing, is shifted to the aspirating position B, which is indicated in phantom lines and in which it is readily accessible exteriorly of the analyser housing. Sample receptacle P is positioned beneath the free lower end of the pipette tube 17 and moved upwardly until the pipette tube dips into the diluted sample.

Double pump 11 is operated with valve 15A open and valve 15B closed and pump 13 draws 4 ml isotonic diluent through conduit 18 while pump 14 draws 20 µl of the diluted sample from sample receptacle P into pipette tube 17. As the aspirated sample volume is extremely small, it fills only a very short length, one or a few centimeters, of the pipette tube.

Sample receptacle P is then attached to beaker mount 31 as shown in full lines to the right in the drawing. Moreover, pipette tube 17 is manually or automatically returned to dispensing position A.

Simultaneously with the drawing of the sample into pipette tube 17 pump 23 is operated with valves 26 and 28 closed so that receiving vessel 20 is emptied of the rinsing liquid that remains from the preceding analysing cycle.

The analyser is then ready for carrying out the remaining part of the analysing process in response to a start signal.

When the start signal is given, double pump 11 dispenses the aspirated sample and the aspirated volume of diluent through pipette tube 17 to receiving vessel 20. Thus, the subsample then held by the receiving vessel will be diluted to 1:40000.

At the same time, dispensing device 33 feeds a predetermined volume, 4 ml for example, of the haemolysing agent through conduit 32 to the remaining portion of the prediluted sample in sample receptacle P. Moreover, air pump 25 is operated with valve 26 open to feed, through conduit 24, air pulses into receiving vessel 20 near the bottom thereof. Air is vented from sample receptacle P through branch conduit 24A and a valve 24B the opening pressure of which is set to a suitable value so that the pressure within sample receptacle P is limited to a predetermined value.

The subsample held in receiving vessel 20, which is diluted to the predetermined higher dilution, is analysed by means of the measuring tube 30 in respect of the number of red blood cells and platelets per unit volume of blood, the size and size distribution of the blood cells or other parameters as desired or required. Thereupon receiving vessel 20 is drained through conduit 22 by means of pump 23.

When receiving vessel 20 is emptied, all or a portion of the haemolysed subsample in sample container P is transferred through conduit 27 to receiving vessel 20 by means of air pump 25. Valve 26 then is in closed position so that the air from the pump is caused to flow through branch conduit 24A into sample receptacle P. The opening pressure of valve 24B and the rate of air flow from pump 25 are set such that the transfer takes place rapidly.

The subsample now held in receiving vessel 20, which is diluted to a predetermined lower dilution, 1:400 for example, is analysed in respect of haemoglobin content, number of white blood cell per unit volume of blood etc., as desired or required.

Then the analysed subsample in receiving vessel 20 is removed through conduit 22 by means of pump 23 whereupon a predetermined quantity of diluent from supply container 19 is introduced into receiving vessel 20 by means of double pump 11. After this diluent has been removed in the same manner as the subsample, a predetermined quantity of diluent is again introduced by means of double pump 11. This diluent is allowed to remain in receiving vessel 20 pending the analysis of the next sample.

As will be understood from the preceding description of an embodiment of the method and apparatus according to the invention, the analysis can be carried out serially with short analysing cycles and using simple means. As soon as the sample has been aspirated from the sample receptacle P, the preparation of the subsample of the lower dilution may begin so that this subsample is ready for analysis as soon as the analysis of the subsample of the higher dilution is completed.

The use of a prediluted sample which is fed into the analyser instead of a sample of undiluted or whole blood minimizes the problems relating to carry-over from one sample to the next.

Naturally, it is within the scope of the invention to automate the method and apparatus to a higher degree than described above with reference to the illustrated exemplary embodiment. For example, the sample receptacles may be fed into and removed from the analyser by automatic means.

The invention is not limited to the multiple dilution which is carried out in the exemplary embodiment. It is within the scope of the invention to carry out the analysis only on the portion of the sample which is diluted only once.

In the embodiment of the invention which is specifically illustrated in the drawing and described above, the relative movements of pipette tube 17 and receiving vessel 20 between the positions for aspirating a predetermined sample volume from sample receptacle P and dispensing this sample volume into receiving vessel 20 are brought about by moving the pipette tube while keeping the receiving vessel stationary. This is the arrangement that is normally preferred, but it is of course within the scope of the invention to arrange for the pipette tube to be stationary and instead arrange for the receiving vessel to move.

We claim:

1. A method for analyzing a fluid sample comprising the steps of:

providing a prediluted sample having a first concentration of sample in a sample container;

aspirating a known volume of said prediluted sample with a pipette disposed in a first position to define a first subsample;

dispensing said first subsample together with a known volume of diluent into a receiving vessel with the pipette disposed in a second position to provide a diluted first subsample having a second, lower concentration of sample in the receiving vessel;

analyzing the diluted first subsample with respect to at least one first sample parameter;

adding a known volume of liquid to a remaining portion of said prediluted sample in the sample container with a liquid dispensing device to provide a diluted sample remaining portion having a third lower concentration of sample in the sample container.

2. A method as difined in claim 1, wherein in said analyzing step, the diluted first subsample is analyzed in the receiving vessel.

3. A method as defined in claim 1, further comprising the steps of:

removing the diluted first subsample from the receiving vessel after analysis;

transferring at least a portion of the remaining portion of the diluted sample from the sample container to the receiving vessel; and analyzing the transferred portion of the remaining portion of the diluted sample with respect to at least one second sample parameter which is the same or different from said first sample parameter.

4. A method as defined in claim 11, wherein the liquid added to the remaining portion to provide the diluted sample remaining portion comprises a reagent.

5. A method as defined in claim 4, wherein said reagent comprises a hemolyzing agent.

6. A method as defined in claim 3, wherein, in said transferring step, transfer is effected by pressurizing the sample container.

7. A method as defined in claim 1, further comprising the step of stirring the diluted first subsample in the receiving vessel by introducing air into the receiving vessel.

8. An apparatus for analyzing a liquid sample comprising:

a receiving vessel for receiving first and second diluted subsamples derived from a prediluted liquid sample to be analyzed;

analyzer means associated with the receiving vessel for analyzing at least one sample parameter of said first and second diluted samples;

a sample container for receiving a prediluted liquid sample having a first concentration of sample;

an aspirating pipette having a sample intake end movable between a first position, wherein the sample intake end is disposed in contact with prediluted liquid sample in said sample container, and a second position, wherein the sample intake end is disposed above or in the receiving vessel;

aspirator means connected with the aspirating pipette for aspirating a known volume of prediluted liquid sample into the pipette when in said first position and for dispensing said aspirated volume and a known volume of liquid diluent from the sample intake end in said second position to deposit a first diluted subsample having a second concentration of sample in said receiving vessel;

means for connecting a fluid dispenser to said sample container for introducing a known volume of liquid into a remaining portion of said prediluted liquid sample in the sample container to define a second diluted subsample having a third concentration of sample in the sample container;

means for transferring at least a portion of said second diluted subsample to the receiving vessel for analysis.

9. An apparatus as defined in claim 8, wherein the at least one sample parameter of the first and second diluted subsamples analyzed by the analyzer means is the same or a different parameter.

10. An apparatus as defined in claim 8, wherein said connecting means sealingly engages an upper end of the sample container.

11. An apparatus as defined in claim 8, wherein said connecting means is connected to a pressure device capable of pressurizing an interior portion of the sample container by introducing air into the interior portion.

12. An apparatus as defined in claim 8, wherein the receiving vessel further comprises means for feeding air into the receiving vessel adjacent a bottom end thereto.

13. An apparatus as defined in claim 8, wherein the aspirating pipette is pivotally movable between the first position and the second position.

14. A method as defined in claim 1, wherein said fluid sample comprises a sample of blood.

15. An apparatus as defined in claim 8, wherein said fluid sample comprises a sample of blood.

16. An apparatus as for analyzing a liquid sample comprising:

a receiving vessel for receiving first and second diluted subsamples derived from a prediluted liquid sample to be analyzed;

an analyzer associated with the receiving vessel capable of analyzing at least one sample parameter of said first and second diluted samples;

a sample container for receiving a prediluted liquid sample having a first concentration of sample;

an aspirating pipette having a sample intake end movable between a first position, wherein the sample intake end is disposed in contact with prediluted liquid sample in said sample container, and a second position, wherein the sample intake end is disposed above or in the receiving vessel;

an aspirator connected with the aspirating pipette to aspirate a known volume of prediluted liquid sample into the pipette when in said first position and to dispense said aspirated volume and a known volume of liquid diluent from the sample intake end in said second position to deposit a first diluted subsample having a second concentration of sample in said receiving vessel;

a connector connecting a fluid dispenser to said sample container for introducing a known volume of liquid into a remaining portion of said prediluted liquid sample in the sample container to define a second diluted subsample having a third concentration of sample in the sample container; and a transfer device capable of transferring at least a portion of said second diluted subsample to the receiving vessel for analysis.

17. An apparatus as defined in claim 16, wherein the at least one sample parameter of the first and second diluted subsamples analyzed by the analyzer is the same or a different parameter.

18. An apparatus as defined in claim 16, wherein said connector sealingly engages an upper end of the sample container.

19. An apparatus as defined in claim 16, wherein said connector is connected to a pressure device capable of pressurizing an interior portion of the sample container by introducing air into the interior portion.

20. An apparatus as defined in claim 16, herein the receiving vessel further comprises an air feeder capable of feeding air into the receiving vessel adjacent a bottom end thereof.

21. An apparatus as defined in claim 16 wherein the aspirating pipette is pivotally movable between the first position and the second position.

* * * * *